(12) United States Patent
Franklin et al.

(10) Patent No.: US 6,323,167 B1
(45) Date of Patent: Nov. 27, 2001

(54) HIGH DI(ALKYL FATTY ESTER) QUATERNARY AMMONIUM COMPOUNDS IN FABRIC SOFTENING AND PERSONAL CARE COMPOSITIONS

(75) Inventors: Ralph Franklin, Danbury, CT (US); Robert Mendello, Peekskill; Paul Albert Iacobucci, Holmes, both of NY (US); Dale Steichen, Göteberg (SE); Phuong-Nga Trinh, Dobbs Ferry; Maurice Dery, Putnam Valley, both of NY (US)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/467,626

(22) Filed: Dec. 20, 1999

Related U.S. Application Data (60) Division of application No. 08/984,830, filed on Dec. 4, 1997, now Pat. No. 6,037,315, which is a continuation-in-part of application No. 08/643,218, filed on May 3, 1996, now Pat. No. 5,916,863.

(51) Int. Cl.$^7$ .............................. A61K 7/075; A61K 7/50; A61K 7/035; A61K 7/06
(52) U.S. Cl. ................ 510/123; 510/138; 510/329; 510/330; 514/880; 424/69; 424/70.1; 424/70.11
(58) Field of Search ..................... 510/123, 138, 510/329, 330; 424/69, 70.1, 70.11; 514/880

(56) References Cited

U.S. PATENT DOCUMENTS

| | | | |
|---|---|---|---|
| 4,339,391 | 7/1982 | Hoffmann et al. | 260/401 |
| 4,429,859 | 2/1984 | Steiner et al. | 252/8.8 |
| 4,456,554 | 6/1984 | Walz et al. | 260/403 |
| 4,767,547 | 8/1988 | Straathof et al. | 252/8.8 |
| 4,789,491 | 12/1988 | Chang et al. | 252/8.75 |
| 4,830,771 | 5/1989 | Ruback et al. | 252/8.8 |
| 4,897,492 | 1/1990 | Bailey, III et al. | 548/352 |
| 4,963,274 | 10/1990 | Ruback et al. | 252/8.75 |
| 5,023,003 | 6/1991 | Yamamura et al. | 252/8.8 |
| 5,066,414 | 11/1991 | Change | 252/8.8 |
| 5,296,622 | 3/1994 | Uphues et al. | 554/103 |
| 5,376,287 | 12/1994 | Borcher et al. | 252/8.8 |
| 5,399,272 | 3/1995 | Swartley et al. | 252/8.8 |
| 5,476,599 | 12/1995 | Rusche et al. | 252/8.8 |
| 5,637,743 | 6/1997 | Contet et al. | 554/52 |
| 6,123,933 * | 9/2000 | Hayama et al. | 424/69 |

FOREIGN PATENT DOCUMENTS

| | | |
|---|---|---|
| 1 163 275 | 3/1984 | (CA) . |
| 43 08 792 | 4/1994 | (DE) . |
| 42 42 480 | 6/1994 | (DE) . |
| 42 43 701 | 6/1994 | (DE) . |
| 0 021 431 | 1/1981 | (EP) . |
| 0 413 249 | 2/1991 | (EP) . |
| 0 483 195 B1 | 5/1992 | (EP) . |
| 0 550 361 A1 | 7/1993 | (EP) . |
| 1 593 921 | 7/1970 | (FR) . |
| 2 160 421 | 12/1985 | (GB) . |
| WO 91/01295 | 2/1991 | (WO) . |
| WO 93 21291 | 10/1993 | (WO) . |
| WO 94/20597 | 9/1994 | (WO) . |
| WO 94/21596 | 9/1994 | (WO) . |

OTHER PUBLICATIONS

Abstract for EP 413–249–A, dated Feb. 20, 1991.
English translation of French Patent No. 1 593 921, published Jul. 10, 1970, pp. 1–8 *Process for treatment of textile products* .
Abstract No. 86–0016 November 1 for GB 2160–421–A, dated Oct. 24, 1985.
Derwent Abstract No. 93–005143/01 for JP 04333667–A, dated Nov. 20, 1992.
Derwent Abstract No. 93–165029/20 for JP 05098571–A, dated Apr. 20, 1993.
English translation of German Patent No. DE 42 42 480, dated Jun. 23, 1994.
Derwent Abstract No. 04220 D/04 for EP 21–431, dated Jan. 7, 1981.

* cited by examiner

Primary Examiner—Mukund J. Shah
Assistant Examiner—Tamthom N. Truong
(74) Attorney, Agent, or Firm—Ralph J. Mancini

(57) ABSTRACT

The present invention generally relates to a textile softening composition which comprises, as the softening agent, a quaternary ammonium salt which comprises a mixture of mono-, di- and tri-ester components, wherein the amount of diester quaternary is greater than about 50% by weight, and the amount of triester quaternary is less than about 25% by weight based on the total amount of quaternary ammonium salt. The invention also relates to a softening agent which comprises a high diester quaternary ammonium salt mixture comprising mono- and diester components derived for ether dialkanolamines. The invention also relates to processes for preparing said softening agents, and methods of use as a fabric softener and as a hair and skin conditioner.

14 Claims, 1 Drawing Sheet

FIGURE 1

HIGH DI(ALKYL FATTY ESTER) QUATERNARY AMMONIUM COMPOUNDS IN FABRIC SOFTENING AND PERSONAL CARE COMPOSITIONS

This is a divisional application of U.S. application Ser. No. 08/984,830, now U.S. Pat. No. 6,037,315, filed Dec. 4, 1997 which is a continuation-in-part of U.S. application Ser. No. 08/643,218 filed May 3, 1996, now U.S. Pat. No. 5,916,863.

FIELD OF THE INVENTION

The present invention generally relates to an improved softening composition containing quaternary ammonium compounds having high diester and low triester content and to a process for preparing same. Compositions of this type have demonstrated unexpectedly superior softening performance and stability compared to compositions of the prior art.

BACKGROUND OF THE INVENTION

Fabric softening compositions suitable for providing fabric softening and static control benefits during laundering are well known in the art. Such compositions generally contain, as the softening component, a substantially water insoluble quaternary ammonium compound having two long alkyl chains.

Further, the use of various quaternized esteramines as fabric softening agents is also known in the art. U.S. Pat. No. 4,339,391 to Hoffmann, et al. for example, discloses a series of quaternized ester-amines which have utility as fabric softeners.

U.S. Pat. No. 5,296, 622 discloses quaternized ester amines having fabric-softening and hydrophilicizing properties which are obtained by reaction of unsaturated fatty acids containing at least 40 mol-% trans-configured double bonds or esters thereof with alkanolamines and subsequent quaternization of the reaction products with alkylating agents.

WO/93/21291 to Henkel claims textile treatment agents containing as a softener, quaternary ammonium compounds with 1, 2 or 3 acyloxyalkyl groups bound to the nitrogen atom. The compounds allegedly have a low viscosity if all or some of the acyl groups are derived from unsaturated fatty acids with a least 30% in the cis form.

U.S. patent No. 5,023,003 to KAO discloses a softener composition which comprises at least one quaternary ammonium salt of the following formulae:

(I)

(II)

(III)

wherein $R^1$ and $R^2$ each represent a hydrocarbon radical having 12–22 carbon atoms, preferably 16–22 carbon atoms and one unsaturated bond; $R^3$ and $R^4$ represent a methyl, ethyl or wherein n is an integer from 1 to 5, and Y is H or methyl; $R^5$ and $R^6$ each represent a hydrocarbon radical having 11–21 carbon atoms and one unsaturated bond; X represents halogen, $CH_3SO_4$, $C_2H_5SO_4$; wherein the stereoisomeric structure of the above said salt includes both the cis-isomer and the trans-isomer with the cis-isomer and the trans-isomer ratio being in the range of from 25/75 to 90/10.

U.S. Pat. No. 4,767,547 discloses fabric softening compositions containing a rapidly biodegradable quaternary ammonium softening agent of the formula:

(I)

wherein:

$R_1$ is $(CH_2)_n$—Q—$T_2$ or $T_3$;

$R_2$ is $(CH_2)_n$—Q—$T_4$ or $T_5$ or $R_3$;

$R_3$ is $C_1$–$C_4$ alkyl;

$T_1, T_2, T_3. T_4, T_5$ are (the same or different) $C_{12}$–$C_{22}$ alkyl or alkenyl;

n is an integer from 1 to 4; and $X^-$ is a softener-compatible anion, the composition having a pH, at 20° C., of from 2.5 to 4.2 upon dilution, in de-ionized water, to a concentration of 0.5% to 1% of said rapidly biodegradable quaternary ammonium compound.

WO 94/20597 to Procter & Gamble relates to softening compounds containing diester quaternary ammonium compounds wherein the fatty acyl groups have an Iodine Value of from greater than about 5 to less than about 100, a cis-trans isomer weight ratio of greater than about 30/70 when the Iodine Value is less than about 25, the level of unsaturation being less than about 65% by weight, wherein said compounds are capable of forming concentrated aqueous compositions with concentrations greater than about 13% by weight at an Iodine Value of greater than about 10 without viscosity modifiers other than normal polar organic solvents present in the raw material of the compound or added electrolyte.

EP 0 550 361 to Stepan discloses cationic fabric treating compositions which comprises quaternary ammonium compounds which are the reaction product of a long chain fatty acid and a tertiary amine wherein the ratio of fatty acid to amine is between 1.85 and 1.4.

WO 91/01295 to Henkel discloses quaternary ammonium compounds useful as textile treatment agents which are prepared by reaction of fatty acids with alkanolamine and thereafter alkylating same to give the quaternary compounds. The esterification reaction is carried out in the presence of an acid catalyst such as hypophosphorous acid. The final product allegedly comprises mono-, di- and triester components in a ratio of 10:62:28%. There is no disclosure, however, of a process for the preparation of a final product having high diester content, i.e., greater than about 55% by weight, and low triester content, i.e., lower than about 20% by weight.

Finally, WO 94/14935 to Henkel discloses concentrated textile softener dispersions containing quaternary ammonium compounds derived from triethanolamine and containing one, two or three fatty acyloxyethyl groups. When the proportion of compounds having two fatty acyloxyethyl groups is larger than 50% by moles, these compounds allegedly have a particularly low viscosity. However, no process to achieve this level of diester was disclosed in this document, and there is no indication of the triester content of the final product.

Therefore, it is clear that the prior art discussed hereinabove does not contemplate or suggest the quaternized diester based softener composition containing high diester content and low triester content. A process for the preparation of such products is also not contemplated.

Accordingly, it is an object of the present invention to provide quaternized esteramine product having high diester content and low triester content. It is a further object of the present invention to provide a textile softening composition which comprises as a major ingredient the quaternary diester compound of the present invention. Another object of the present invention is to provide a textile softening composition which is non-yellowing and has improved softening performance and desirable textile softening properties such as improved softener biodegradability, viscosity, water absorbency, stability and the like. Finally, it is an object of the present invention to provide a hair care composition which comprises as a major ingredient the quaternary diester compound of the present invention. These and other objects are readily apparent from the following disclosure.

SUMMARY OF THE INVENTION

The present invention generally relates to a textile softening composition which comprises, as the softening agent, a quaternary ammonium salt which comprises a mixture of mono-, di- and tri-ester components, wherein the amount of diester quaternary is greater than about 55% by weight, and the amount of triester quaternary is less than about 20% by weight based on the total amount of quaternary ammonium salt. The invention also contemplates a softening agent which comprises a high diester content quaternary ammonium ester which is derived from an ether alkanol amine. Methods for preparing said softening agents, and to personal care compositions which incorporate same are also within the scope of the present invention.

DETAILED DESCRIPTION OF THE INVENTION

The present invention generally relates to a textile softening and/or personal care compositions which comprise quaternary ammonium based softening agents which are high in diester and low in triester content and to a process for the preparation of same. Quaternary ammonium compounds having particularly good performance and stability profiles are obtained by reaction of $C_{12}$–$C_{22}$ fatty acids or the hydrogenation products thereof, or a mixture of such acids, with an alkanolamine in the presence of an acid catalyst, wherein the ratio of fatty acid to alkanolamine is from about 1.40–2.0. The resultant esteramine reaction products are subsequently quaternized to obtain the quaternary ammonium salts of the present invention.

The fatty acid is preferably a $C_{16}$–$C_{22}$ acid containing a degree of unsaturation such that the iodine value ("IV") is in the range of from about 3–90, preferably, from about 20–90, more preferably in the range of 40–60 and still more preferably, in a range of from about 45–55. Preferred fatty acids include but are not limited to oleic, palmitic, erucic, eicosanic and mixtures thereof. Soy, tallow, palm, palm kernel, rape seed, lard, mixtures thereof and the like are typical sources for fatty acid which can be employed in the present invention. Partial hydrogenation can be employed, if required, to minimize the polyunsaturate levels in order to improve the stability (e.g., odor, color, etc.) of the final product. It is also preferred that the fatty acid(s) employed in the present process have a cis to trans isomer ratio of from about 80:20 to about 95:5. More preferably, the trans isomer content of said fatty acid(s) is less than about 10%. An optimum trans-isomer content is between about 0.5–9.9%. The most preferred fatty acid is a mixture of tallow/distilled tallow having a cis:trans isomer ratio of greater than 9:1.

The alkanolamines employable in the present invention generally correspond to the general formula:

herein R, $R_1$ and $R_2$ are independently selected from $C_2$–$C_6$ hydroxyalkyl groups. Preferred alkanolamines include but are not limited to triethanolamine, propanol diethanolamine, ethanol diisopropanolamine, triisopropanol amine, diethanolisopropanol amine, diethanolisobutanolamine and mixtures thereof.

The molar ratio of fatty acid to alkanol amine is generally in the range of from about 1.4 to 2.0, preferably from about 1.55–1.90, and more preferably, in the range of from about 1.65–1.75. Best results are usually obtained when the molar ratio is between about 1.68–1.72. The acid catalyst employable in the present process includes, but is not limited to, acid catalysts such as sulphonic acid, phosphorous acid, p-toluene sulphonic acid, methane sulphonic acid, oxalic acid, hypophosphorous acid or an acceptable Lewis acid in an amount of 500–3000 ppm based on the amount of fatty acid charge. A preferred acid catalyst is hypophosphorous acid. Typically, 0.02–0.2% by weight, and more preferably 0.1 to 0.15% by weight of acid catalyst, based on the weight of fatty acid, in employed in the present process.

The esterification of fatty acids with alkanolamines is carried out at a temperature of from about 170°–250° C. until the reaction product has an acid value of below 5. After the esterification, the crude product is reacted with alkylating agents in order to obtain the quaternary ammonium product. Preferred alkylating agents include $C_1$–$C_3$ straight or branched chain alkyl halides, phosphates, carbonates, or sulfates, $C_7$–$C_{10}$ aralkyl halides, phosphates or sulfates, and mixtures thereof. Examples of preferred alkylating agents include but are not limited to methyl chloride, benzyl chloride, diethyl sulfate, dimethyl carbonate, trimethyl phosphate, dimethyl sulfate or mixtures thereof. Choosing the type and amount of alkylating agent employed is well within the skill of one in the art. Typically, when dimethyl sulfate is the alkylating agent, 0.7 to 1.0, preferably 0.75 to 0.98 mol dimethyl sulfate per mole of esteramine is satisfactory in yielding the quaternized product.

While such esterquats are typically prepared by reaction of the corresponding esteramine with dimethyl sulfate, applicants have discovered a particularly valuble improvement to conventional quaternization processes. Dimethyl sulfate, a strong alkylating agent, is typically employed because of the excessively long reaction times encountered when weaker alkylating agents, such as methyl chloride, are employed. The present inventors have, however, unexpectedly discovered that the quaternization reaction time can be significantly reduced, in many cases by 50% or more, if the esteramine mixture to be quaternized contains minimal amounts of triester component. More particularly, the present inventors have unexpectedly found that by modifying esterification conditions, they can minimize the amount of triesteramine component formed in the esteramine mixture. Reducing the amount of triester component, by even a relatively small amount, can lead to a significant reduction in quaternization reaction time. This allows one to utilize weaker alkylating agents, such as methyl chloride, which is less expensive and less toxic, without the disadvantage of excessively long reaction times. Further, the performance of the final product is in no way impaired and, in fact, an improvement in performance is typical. Similar improvements with other alkylating agents have been observed.

Triester formation in the esteramine mixture can be minimized by accelerating the heat up rate in the esterification reaction of fatty acids with alkanolamines. Typically, the accelerated heat up rate of greater than about 0.4° C./minute, more preferably greater than about 0.8° C./minute, and still more preferably greater than about 1.25° C./minute from a temperature of about 70° C. to a temperature in a range of from between 170° C. to 250° C. is effective in minimizing triester formation in the esteramine mixture.

The quaternization may be carried out in bulk or in solvent, at temperatures ranging from 60°–120° C. If a solvent is employed, then the starting materials and/or product must be soluble in the solvent to the extent necessary for the reaction. Solvents of this type are generally known in the art. Suitable examples include polar solvents such as, for example, lower alcohols, i.e., $C_1$–$C_6$ alcohols. Other solvents which can be employed include, but are not limited to mono-, di-, and tri-glycerides, fatty acids, glycols and mixtures thereof.

A resultant quaternary ammonium salt comprises a mixture mono- (I), di- (II) and tri-ester (III) components of the following formulae:

(I)

(II)

(III)

wherein:
X, X' and X" are the same or different and are selected from straight or branched chain, optionally substituted oxyalkylene or polyoxyalkylene groups having from 2–6 carbon atoms, preferably 3–6 carbon atoms, where the oxyalkylene units number from about 1–10, preferably 1–5, and still more preferably 1–2; each R group is individually selected from straight or branched chain, optionally substituted alkyl groups having from 11 to 23 carbon atoms, Y is an alkylphenyl group or a straight or branched chain optionally substituted $C_1$ to $C_6$ alkyl or alkylene group; and $Z^-$ represents a softener compatible anion including but not limited to halogen, $CH_3SO_4$ or $C_2H_5SO_4$.

The reaction products may also contain minor amounts of methyl trialkanolammonium salts and other impurities. The amount of diester in the final product (II) is generally greater than about 55% by weight and the amount of triester (III), based on the gas chromatagraph of the esteramine, is generally less than about 25%, preferably less than 20% by weight based on the total amount of quaternary ammonium salt product.

Typical product compositions contemplate an ester distribution within the following ranges: greater than about 55wt % diester and less than about 25 wt % triester, with a total fatty acid IV of from about 20 to about 90; more preferably, greater than about 60 wt % diester and less than about 20 wt % triester, with a total IV of from about 30 to about 70; and still more preferably, greater than about 62 wt % diester and less than about 17 wt % triester, with a total IV of from about 40 to about 60. In a most preferred embodiment, the IV is between about 45 to about 58.

The ratio of cis to trans double bonds of the above salts is preferably in the range of from about 80:20 to about 95:5. Preferably, the cis:trans ratio is greater than about 90:10. In a most preferred embodiment, the amount of trans isomer ideally in the range of from 5 to 9.5%.

There are several convenient methods for obtaining the desired cis:trans ratio of the quaternary ammonium salt product. The preferred method is to produce the quaternary ammonium salt from a cis-isomeric and trans-isomeric fatty acids after adjusting said acids to the desired ratio.

Another method is to produce the quaternary ammonium salt from the mixture after adjusting the ratio thereof by isomerizing a portion of the cis-isomeric fatty acid or ester thereof into the trans-isomer, in the presence of a metallic catalyst. Other methods are readily apparent to and well within the skill of one of ordinary skill in the art.

The quaternary ammonium compounds according to the present invention can generally be prepared by reacting at least one $C_{12}$–$C_{22}$ fatty acid having a IV of from 20–90 with an alkanol amine in the presence of an acid catalyst. The ratio of acid to amine is preferably in the range of 1.4 to 2.0, and the reaction is carried out at a temperature of from about 170° C. to about 250° C. until the reaction product has an acid value of below about 5. A heat up rate of at least about 0.8° C. per minute is employed in order to minimize triester formation. The esterification products are subsequently alkylated in order to obtain the quaternary ammonium product.

In another embodiment, the present invention contemplates a family of quaternary ammonium esters which are derived from ether alkanolamines. Said quaternary ammonium esters are of the general formula:

(IV)

wherein:
n is an integer of 1 or 2, R is a $C_5$ to $C_{23}$ straight or branched chain, optionally substituted alkyl group, each X can be the same or different and is selected from straight or branched chain, optionally substituted oxyalkylene or polyoxyalkylene groups having from 2–6 carbon atoms; each Q can be the same or different and is selected from a oxyalkylene or polyoxyalkylene group, or a straight or branched chain, optionally substituted alkyl, alkylene, alkylphenyl, hydroxyalkyl, hydroxyalkylene, wherein at least one of said Q groups is a $C_2$ to $C_6$ linear or branched chain oxyalkylene or polyoxyalkylene capped with a $C_1$ to $C_6$ alkyl, or an alkyl phenyl group; and $Z^-$ is a compatible anion.

The above esterquat is generally prepared by reacting a fatty acid and/or fatty acid methyl ester as previously defined herein with an ether alkanolamine. The reaction is essentially the same as the reaction of said acid and/or said acid ester with an alkanolamine previously described herein, with an exception that the employment of a minimum heat up rate in order to acheive a high diester, low triester containing product is not necessary. More particularly, the reaction of fatty acid or fatty acid methyl ester with an ether alkanolamine produces only mono- and di-substituted ester products. This is because the ether group is non-reactive and does not lead to the formation of a tri-substituted species. Accordingly, the heat up rate which is an important requirement of the trialkanolarnine based process is less important when ether alkanolamines are employed as a reactant since the formation of tri-substituted species is not possible.

Further, employment of ether alkanolamines is beneficial in that they are more reactive with a broader range of alkylating agents, and the final products are easier to formulate and are more storage stable. Finally, the ratio of mono- and di-substituted species can be controlled by controlling the ratio of fatty acid/fatty acid methyl ester to ether alkanolamine.

A exemplary process for the preparation of a high diester quaternary ammonium mixture comprises reacting:

I.) a $C_{11}$–$C_{23}$ substituted or unsubstituted fatty acid or mixture of fatty acids having an Iodine Value of from about 20 to about 90, and having less than about 20% trans double bonds, with II) an ether alkanolamine of the formula:

wherein R is a $C_2$–$C_6$ alkyl ether, and each of $R_1$ and $R_2$ is independently selected from $C_2$–$C_6$ hydroxyalkyl groups, wherein the molar ratio of said fatty acid to ether alkanol amine is from about 1.4 to about 2.0, preferably from about 1.6–1.9, and quaternizing the resultant esteramine mixture in order to obtain an improved high diester quaternary ammonium mixture.

Preferred ether alkanolamine are selected from the group consisting of methoxyethyldiethanolamine, methoxypropyldiethanolamine, methoxybutyldiethanolamine and mixtures thereof. The high diester quaternary ammonium mixture derived from ether alkanolamines in accordance with the present invention generally has a diester content of at least 70 wt %, preferably greater than about 75 wt %, and still more preferably, greater than about 80 wt % on a 100 wt % active basis.

The textile softening compositions of the present invention having high diester content and low triester content demonstrate superior performance compared to typical esteramine quaternary compounds, and the excellent color and odor stability allows the formulator greater latitude in preparing high quality softening products.

The compositions can be aqueous liquids, preferably concentrated, containing from about 4–50%, preferably from about 10 to 45% and still more preferably from about 15–40% by weight of the quaternary ammonium compounds of the present invention. The compositions of the present invention can be further concentrated to particulate solids containing from about 50–95%, preferably 60–90% quaternary ammonium softening compound, if desired.

Water can be added to the particulate solid compositions to form either dilute or concentrated liquid textile softening compositions according to the invention. The solid particulate composition can also be directly added to the rinse bath in order to provide an adequate usage concentration, which is typically in the range of from about 10–1000 ppm, more preferably, in a range of from about 50–500 ppm. A standard rinse-cycle softening composition in accordance with the present invention can be prepared by preheating water to a temperature of from about 45°–60° C. in a suitable vessel and acidifying same to a pH of from about 2.7–3.2. The warmed quaternary ammonium salt is thereafter added to the acidified water with agitation while the temperature is maintained at 45° C.–60° C. Fragrance and other optional ingredients can then be solubilized into the softener dispersion, and the weight is thereafter adjusted with deionized water. Dispersions such as this are typically storage stable within a temperature range of from about 4° C. to about 50° C.

Although the stability of the textile softening compositions of the present invention is such that stabilizing cosurfactants are not required, they may nevertheless be included along with a wide variety of other optional ingredients. A brief non-limiting description of some of the optional ingredients which may be employed in the textile softening compositions of the present invention is provided below.

I.) Viscosity/Dispersibility Aids

As previously mentioned, relatively concentrated compositions of the quaternary esters of the present invention can be prepared that are stable, without the addition of concentration aids. However, the compositions of the present invention may require organic and/or inorganic concentration aids to go to even higher concentrations and/or to meet higher stability standards depending on the other ingredients. These concentration aids which are typically viscosity modifiers may be needed, or preferred, for ensuring stability under extreme conditions when particular softener active levels in relation to IV are present.

Surfactant Concentration Aids

Surfactant concentration aids typically fall into four catagories:
(1) mono long chain alkyl cationic surfactants;
(2) nonionic surfactants;
(3) amine oxides; and
(4) fatty acids.

Mixtures of the aforementioned surfactant concentration aids can, of course, also be employed.

(1) Mono-Long Chain Alkyl Cationic Surfactants

Preferred mono-long chain alkyl or ester based water-soluble cationic surfactants generally fall within the scope of the following general formula:

[R²N⁺(R)₃]X⁻ wherein the $R^2$ group is $C_{12}$–$C_{22}$ hydrocarbon group, preferably $C_{12}$–$C_{18}$ alkyl group or the corresponding ester linkage interrupted group with a short chain alkylene ($C_1$–$C_6$) group between the ester linkage and the N, and having a similar hydrocarbon group. Each R is a $C_1$–$C_6$ unsubstituted or substituted alkyl (e.g., by hydroxy) or hydrogen, preferably methyl, and the counterion X- is a softener compatible anion such as, for example, chloride, bromide, methyl sulfate, etc.

The cationic surfactants, if present, are usually added to solid compositions at a level of from 0% to about 15%, preferably from about 3% to about 15%, more preferably from about 5% to about 15%. In liquid compositions they are usually employed at level of from 0% to about 15%, preferably from about 0.5% to about 10%. In general, the total amount single-long-chain cationic surfactant is added in an amount effective to obtain a stable composition.

The foregoing levels represent the amount of the single-long-chain-alkyl cationic surfactant which is added to the composition of the present invention. The ranges do not include the amount of monoester which is already present in the diester quaternary ammonium compound.

The long chain group $R^2$, of the single-long-chain-alkyl cationic surfactant generally contains an alkylene group having from about 10 to about 22 carbon atoms, preferably from about 12 to about 16 carbon atoms for solid compositions, and preferably from about 12 to about 18 carbon atoms for liquid compositions. This $R^2$ group can be attached to the cationic nitrogen atom through a group containing one, or more, ester, amide, ether, amine, etc., preferably ester, linking groups which can be desirable for increased hydrophilicity, biodegradability, etc. Such linking groups are preferably within about three carbon atoms of the nitrogen atom. Suitable biodegradable single-long-chain alkyl cationic surfactants containing an ester linkage in the long chain are described in U.S. Pat. No. 4,840,738 which is incorporated herein by reference. If the corresponding, non-quaternary amines are used, any acid (preferable a mineral or polycarboxylic acid) which is added to keep the ester groups stable will also keep the amine protonated in the compositions and preferably during the rinse so that the amine has a cationic group. The composition is buffered (pH from about 2 to about 5, preferably from about 2 to about 4) to maintain an appropriate, effective charge density in the aqueous liquid concentrate product and upon further dilution e.g., to form a less concentrated product and/or upon addition to the rinse cycle of a laundry process.

The main function of the water-soluble cationic surfactant is to lower the viscosity and/or increase the dispersibility of the diester softener and it is not, therefore, essential that the cationic surfactant itself have substantial softening properties, although this may be the case. Also, surfactants having only a single long alkyl chain, presumably because they have greater solubility in water, can protect the diester softener from interacting with anionic surfactants and/or detergent builders that are carried over into the rinse. Other cationic materials with ring structures such as alkyl imidazoline, imidazolimium, pyridine, and pyridinium salts having a single $C_{12}$–$C_{30}$ alkyl chain can also be used. Some alkyl imidazolinium salts useful in the present invention have the general formula:

wherein $y^2$ is —C(O)—O—, —O—(O)C—, —C(O)—N(R⁵), or —N(R⁵)—C(O)— in which $R^5$ is hydrogen or a $C_1$–$C_4$ alkyl radical; $R^6$ is a $C_1$–$C_4$ alkyl radical; $R^7$ and $R^8$ are each independently selected from R and $R^2$ as defined hereinbefore for the single-long-chain cationic surfactant with only one being $R^2$. Some alkyl pyridinium salts useful in the present invention have the general formula:

wherein $R^2$ and $X^-$ are as defined above. A typical material of this type is cetyl pyridinium chloride.

(2) Nonionic Surfactants—Alkoxylated Materials.

Nonionic surfactants suitable as viscosity/dispersibility modifiers include the addition products of ethylene and/or propylene oxide with fatty alcohols, fatty acids, fatty amines, etc. Any of the alkoxylated materials hereinafter described can be used as the nonionic surfactant. In general terms, the nonionics herein can be employed in solid compositions at a level of from about 5% to about 20%, preferably from about 8% to about 15%, and in liquid compositions at a level of from 0% to about 5%, preferably from about 0.1% to about 5%, more preferably from about 0.2% to about 3%.

Suitable water-soluble nonionic surfactants generally fall within the scope of the following general formula:

R²—Y—(C₂H₄O)_zC₂H₄OH wherein $R^2$ for both solid and liquid compositions is selected from the group consisting of primary, secondary and branched chain alkenyl hydrocarbyl groups; and primary, secondary and branched chain alkyl- and alkenyl-substituted phenolic hydrocarbyl groups; said hydrocarbyl groups having a hydrocarbyl chain length of from about 8 to about 20, preferably from about 10 to about 18 carbon atoms. More preferably the hydrocarbyl chain length for liquid compositions is from about 16 to about 18 carbon atoms and for solid compositions from about 10 to about 14 carbon atoms.

In the general formula for the ethoxylated nonionic surfactants herein, Y is typically —O—, —C(O)—, —C(O)N(R)—, or —C(O)N(R)R—, wherein R, when present, has the meanings given hereinbefore, and/or R can be hydrogen, and z is at least about 8, preferably at least about 10–11. Performance, and usually stability of the softener composition decrease when fewer ethoxylate groups are present.

The nonionic surfactants herein are characterized by an HLB (hydrophilic-lipophilic balance) of from about 7 to about 20, preferably from about 8 to about 15. By defining $R^2$ and the number of ethoxylate groups, the HLB of the surfactant is, for the most part, determined. However, it is preferred that for concentrated liquid compositions, the nonionic surfactants contain relatively long chain $R^2$ groups and are relatively highly ethoxylated. While shorter alkyl chain surfactants having short ethoxylated groups may possess the requisite HLB, they are not as effective. Nonionic surfactants as the viscosity/dispersibility modifiers are preferred over the other modifiers disclosed herein for compositions with higher levels of perfume.

Nonionic surfactants employable in the present invention include but are not limited to the following examples. In the examples, the number of ethoxyl groups in the molecule (EO) is defined by an integer.

(i) Straight-Chain, Primary Alcohol Alkoxylates

The deca-, undeca-, dodeca-, tetradeca-, and pentadeca-ethoxylates of n-hexadecanol, and n-octadecanol having an HLB within the preferred range are useful as viscosity/dispersibility modifiers of the context of this invention. Preferred examples of ethoxylated primary alcohols useful herein as the viscosity/dispersibility modifiers of the compositions include but are not limited to n-$C_{18}$EO(10); and n-$C_{10}$EO(11). The ethoxylates of mixed natural or synthetic alcohols in the "tallow" chain length range are also useful herein. Specific examples of such materials include tallow alcohol-EO(11), tallow alcohol-EO(18), and tallow alcohol-EO(25).

(ii) Straight-Chain, Secondary Acohol Alkoxylates

The deca-, undeca-, dodeca-, tetradeca-, pentadeca-, octadeca-, and nonadecaethoxylates of 3-hexadecanol, 2-octadecanol, 4-eicosanol, and 5-eicosanol having an HLB within the preferred range are useful viscosity/dispersibility modifiers in the context of the present invention. Examples of ethoxylated secondary alcohols useful herein as the viscosity/dispersibility modifiers of the compositions include but are not limited to: 2-$C_{16}$EO(11); 2-$C_{20}$EO(11); and 2-$C_{16}$EO(14).

(iii) Alkyl Phenol Alkoxylates

As is the case of the alcohol alkoxylates, the hexa- through octadeca-ethoxylates of alkylated phenols, particularly monohydric alkylphenols, having an HLB within the preferred range are useful as the viscosity/dispersibility modifiers. The hexa- through octadeca-ethoxylates of p-tridecylphenol, m-pentadecylphenol, and the like, are useful herein. Preferred examples of ethoxylated alkylphenols useful as the viscosity/dispersibility modifiers include but are not limited to: p-tridecylphenol EO(11) and p-pentadecylphenol EO(18).

It would be generally recognized by one of ordinary skill in the art that a phenylene group in the nonionic formula is the equivalent of an alkylene group containing from 2 to 4 carbon atoms. For present purposes, nonionic surfactants containing a phenylene group are considered to contain an equivalent number of carbon atoms calculated as the sum of the carbon atoms in the alkyl group plus about 3.3 carbon atoms for each phenylene group.

(iv) Olefinic Alkoxylates

The alkenyl alcohols, both primary and secondary, and alkenyl phenols corresponding to those disclosed hereinabove can be ethoxylated to an HLB within the range recited herein and used as the viscosity/dispersibility modifiers in the compositions of the present invention.

(v) Branched Chain Alkoxylates

Branched chain primary and secondary alcohols which are available from the well-known "OXO" process can be ethoxylated and employed as the viscosity/dispersibility modifiers in the present compositions.

The ethoxylated nonionic surfactants summarized hereinabove can be usefully employed in the present compositions either alone or in specific mixtures.

(3) Amine Oxides

Suitable amine oxides include but are not limited to those with one alkyl or hydroxyalkyl moiety of about 8 to about 28 carbon atoms, preferably from about 8 to about 16 carbon atoms, and two alkyl moieties selected from the group consisting of alkyl groups and hydroxyalkyl groups with about 1 to about 3 carbon atoms. Amine oxides, if employed, are generally present in solid compositions at a level of from 0% to about 15%, preferably from about 3% to about 15%; and in liquid compositions at a level of from 0% to about 5%, preferably from about 0.25% to about 2%. The total amount amine oxide is generally present in an amount effective to provide a stable composition.

Preferred examples of amine oxides employable in the present invention include but are not limited to dimethyloctylamine oxide, diethyldecylamine oxide, bis-(2-hydroxyethyl)dodecylamine oxide, dimethyl dodecylamine oxide, dipropyltetradecylamine oxide, methylethylhexadecylamine oxide, dimethyloctadecylamine oxide, di(2-hydroxyethyl)octyldecylamine oxide and coconut fatty alkyl dimethylamine oxide.

(4) Fatty Acids and/or Alkoxylated Fatty Acids

Suitable fatty acids include those containing from about 12 to about 25, preferably from about 13 to 22, more preferably from about 16 to about 20, total carbon atoms, with the fatty moiety containing from about 10 to about 22, preferably from about 10 to about 18, more preferably from about 10 to about 14 carbon atoms. Fatty acids are typically present at approximately the levels outlined above for amine oxides. Fatty acids are preferred concentration aids for those compositions which require a concentration aid and contain perfume.

Alkoxylated fatty acids prepared by reaction alkylene oxide with the aforementioned fatty acids can also be preferably employed in the compositions of the present invention.

Electrolyte Concentration Aids

Inorganic viscosity control agents which can also act like or augment the effect of the surfactant concentration aids include water-soluble, ionizable salts. Such salts can also optionally be incorporated into the compositions of the present invention. A wide variety of ionizable salts can be used. Examples of suitable salts include but are not limited to the halides of the Group IA and IIA metals of the Periodic Table of Elements, e.g., calcium chloride, magnesium chloride, sodium chloride, potassium bromide, and lithium chloride. The ionizable salts are particularly useful during the process of mixing the ingredients to make the compositions herein, and to obtain the desired viscosity. The amount of ionizable salts used depends on the amount of active ingredients used in the compositions. Typical levels of salts used to control the composition viscosity are from about 20 to about 20,000 parts per million (ppm), preferably from about 20 to about 11,000 ppm, by weight of the composition.

Alkylene polyammonium salts can be incorporated into the composition to give viscosity control in addition to, or in place of, the water-soluble, ionizable salts described above. Additionally, these agents can act as scavengers, forming ion pairs with anionic detergent carried over from the main wash to the rinse and may improve softening performance. These agents may stabilize the viscosity over a broader range of temperature, especially at low temperatures, compared to the inorganic electrolytes. Specific examples of alkylene polyammonium salts include but are not limited to 1-lysine monohydrochloride and 1,5-diammonium-2-methylpentane dihydrochloride.

II) Stabilizers

Stabilizers may also be optionally employed in the compositions of the present invention. The term "stabilizer," as used herein, includes antioxidants and reductive agents. These agents are typically present at levels of from 0% to about 2%, preferably from about 0.01% to about 0.2%, more preferably from about 0.05% to about 0.1% for antioxidants and more preferably from about 0.01% to about 0.2% for reductive agents. Stabilizer use assures good odor stability under long term storage conditions. Further, use of antioxidants and reductive agent stabilizers is especially critical for unscented or low scent products.

Examples of antioxidants which can be employed in the compositions of the present invention include but are not limited to a mixture of ascorbic acid, ascorbic palmitate, propyl gallate, available from Eastman Chemical Products, Inc., under the trade names Tenox® PG and Tenox S-1; a mixture of BHT (butylated hydroxytoluene), BHA (butylated hydroxyanisole), propyl gallate, and citric acid, available from Eastman Chemical Products, Inc., under the trade name Tenox-6;butylated hydroxytoluene, available from UOP Process Division under the trade name Sustane® BHT; tertiary butylhydroquinone available from Eastman Chemical Products, Inc. under the mark Tenox® TBHQ; natural tocopherols available from Eastman Chemical Products, Inc. under the mark Tenox® GT-1/GT-2; and butylated hydroxyanisole available from Eastman Chemical Products, Inc., as BHA; long chain esters ($C_8$–$C_{22}$) of gallic acid such as dodecyl gallate; irganox 1010; Irganox® 1035; Irganox® B 1171; Irganox® 1425; Irganox® 3114; Irganox ® 3125; and mixtures thereof; or in combination with citric acid and/or EDTA or other chelators such as isopropyl citrate, Dequest® 2010 available from Monsanto under the name 1-hydroxyethylidene-1,1-diphosphonic acid (etidronic acid), Tiron®, available from Kodak with a chemical name of 4,5-dihydroxy-m-benzene-sulfonic acid/sodium salt, and DTPA® (diethylenetriaminepentaacetic acid), available from Aldrich. The chemical names and CAS numbers for some of the above stabilizers are tabulated below.

| Anti-oxidant | CAS No. | Chemical Name used in Code of Federal Regulations |
|---|---|---|
| Irganox ® 1010 | 6683-19-8 | Tetrakis [methylene(3,5-di-tert-butyl-4 hydroxyhydrocinnamate)] methane |
| Irganox ® 1035 | 41484-35-9 | Thiodiethylene bis(3,5-di-tert-butyl-4-hydroxyhydrocinnamate |
| Irganox ® 1098 | 23128-74-7 | N,N'-hexamethylene bis(3,5-di-tert-butyl-4-hydroxy hydrocinnammamide |
| Irganox ® B 1171 | 31570-04-4 23128-74-7 | 1:1 Blend of Irganox ® 1098 and Irgafos ® 168 |
| Irganox ® 1425 | 65140-91-2 | Calcium bis[monoethyl(3,5-di-tert-butyl-4-hydroxybenzyl)phosphonate] |
| Irganox ® 3114 | 27676-62-6 | 1,3,5-Tris (3,5-di-tert-butyl-4-hydroxybenzyl)-s-triazine-2,4,6-(1H, 3H, 5H)trione |
| Irganox ® 3125 | 34137-09-2 | 3,5-Di-tert-butyl-4-hydroxy-hydrocinnamic acid triester with 1,3,5-tris(2-hydroxyethyl)-S-triazine-2,4,6-(1H, 3H, 5H)-trione |
| Irgafos ® 168 | 31570-04-4 | Tris(2,4-di-tert-butyl-phenyl)phosphite |

Examples of reductive agents include but are not limited to sodium borohydride, sodium bisulfite, hypophosphorous acid, and mixtures thereof. The stability of the compounds and compositions herein can be improved by use of stabilizers, but in addition, the preparation of compounds used herein and the source of hydrophobic groups can be important. Surprisingly, some highly desirable, readily available sources of hydrophobic groups such as fatty acids from, e.g., tallow, possess odors that remain with the compound despite the chemical and mechanical processing steps which convert the raw tallow to finished product. Such sources must be deodorized, e.g., by absorption, distillation, stripping, etc., as is well known in the art. In addition, contact of the resulting fatty acyl groups to oxygen and/or bacteria must be minimized by adding antioxidants, antibacterial agents, etc.

ADDITIONAL OPTIONAL INGREDIENTS

Soil Release Agent

The composition of the present invention may optionally contain from 0.1% to 10%, preferably from 0.2% to 5%, of a soil release agent. Preferably, the soil release agent is a polymeric soil release agent such as one which contains copolymeric blocks of terephthalate and polyethylene oxide or polypropylene oxide, cationic guar gums, and the like. U.S. Pat. No. 4,956,447, which is incorporated herein by reference, discloses some preferred soil release agents comprising cationic functionalities.

A preferred soil release agent is copolymer having blocks of terephthalate and polyethylene oxide which are comprised of repeating units of ethylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weights of from about 300 to about 2,000. The molecular weight of this polymeric soil release agent is in the range of from about 5,000 to about 55,000.

Another preferred polymeric soil release agent is a crystallizable polyester with repeat units of ethylene terephthalate units containing from about 10% to about 15% by weight of ethylene terephthalate units together with from about 10% to about 50% by weight of polyoxyethylene glycol of average molucular weight of from about 300 to about 6,000, wherein the molar ratio of ethylene terephthalate units to polyoxyethylene terephthalate units in the crystallizable polymeric compound is between 2:1 and 6:1. Examples of this polymer include but are not limited to Zelcon® 4780 available from DuPont and Milease® T available from ICI. Highly preferred soil release agents are polymers of the generic formula (I):

(I)

in which X can be any suitable capping group, wherein each X is selected from the group consisting of H, and alkyl or acyl groups containing from about 1 to about 4 carbon atoms, wherein methyl is preferred. n is selected for water solubility and is generally from about 6 to about 113, preferably from about 20 to about 50. u is critical to liquid formulations having a relatively high ionic strength. The amount of material wherein u is greater than 10 should be minimized, while there should be at least 20%, preferably at least 40%, of material in which u ranges from about 3 to about 5.

The $R^1$ moieties are essentially 1,4-phenylene moieties. As used herein, the term "the $R^1$ moieties are essentially 1,4-phenylene moieties" refers to compounds where the $R^1$ moieties consist entirely of 1,4-phenylene moieties, or are partially substituted with other arylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphtylene, 1,4-naphthylene, 2,2-biphenylene, 4,4-biphenylene and mixtures thereof. Alkylene and alkenylene moieties which can be partially substituted include ethylene, 1,2-propylene, 1,4-butylene, 1,5-pentylene, 1,6-hexamethylene, 1,7-heptamethylene, 1,8-octamethylene, 1,4-cyclohexylene, and mixtures thereof.

For the $R^1$ moieties, the degree of partial substitution with moieties other than 1,4-phenylene should be such that the soil release properties of the compound are not adversely affected to a significant degree. Generally, the degree of partial substitution which can be tolerated will depend upon the backbone length of the compound, with longer backbones generally having greater partial substitution for 1,4-phenylene moieties. Usually, compounds where the $R^1$ comprise from about 50% to about 100% 1,4-phenylene moieties (from 0 to about 50% moieties other than 1,4-phenylene) have adequate soil release activity. For example, polyesters with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $R^1$ moieties consist entirely of (i.e., comprise 100%) 1,4-phenylene moieties, i.e., each $R^1$ moiety is 1,4-pheneylene.

For the $R^2$ moieties, suitable ethylene or substituted ethylene moieties include but are not limited to ethylene, 1,2-propylene, 1,2-butylene, 1,2-hexylene, 3-methoxy-1,2-propylene and mixtures thereof. Preferably, the $R^2$ moieties are essentially ethylene moieties, 1,2-propylene moieties or mixtures thereof. Inclusion of a greater percentage of ethylene moieties tends to improve the soil release activity of compounds. Inclusion of a greater percentage of 1,2-propylene moieties tends to improve the water solubility of the compounds.

The use of 1,2-propylene moieties or a similar branched equivalent is desirable for incorporation of any substantial part of the soil release component in the liquid fabric softener compositions. Preferably, from about 75% to about 100%, more preferably from about 90% to about 100%, of the $R^2$ moieties are 1,2-propylene moieties. The value for each n is at least about 6, and preferably is at least about 10.

The value for each n usually ranges from about 12 to about 113. Typically, the value for each n is in the range of from about 12 to about 43.

Cellulosic derivatives are also functional as soil release agents. Examples of such agents include but are not limited to hydroxyethers of cellulose such as Methocel® available from Dow Chemical; and certain cationic cellulose ether derivatives such as Polymer JU-125®, JR-400®, and JR-30M® available from Union Carbide. Additional examples of cellulosic polymeric soil release agents include methyl cellulose, hydroxypropyl methylcellulose, hydroxybutyl methylcellulose, or mixtures thereof wherein said cellulosic polymer has a viscosity in a 2% aqueous solution at 20° C. of 15 to 75,000 centiposie. Other effective soil release agents are cationic guar gums such as Jaguar Plus® available from Stein Hall and Gendrive 458® available from General Mills. A more complete disclosure of highly preferred soil release agents is contained in European Patent Application No. 185,427 to Gosselink which was published Jun. 25, 1986, and U.S. Pat. No. 5,207,933 to Trinh et al. which issued May 4, 1993, both of which are incorporated herein by reference.

Bacteriocides

Examples of bacteriocides which can be employed in the compositions of the present invention include but are not limited to parabens such as methyl, glutaraldehyde, formaldehyde, 2-bromo-2-nitropropane-1,3-diol sold by Inolex Chemicals under the trade name Bronopol®, and a mixture of 5-chloro-2-methyl-4-isothiazoline-3-one and 2-methyl-4-isothiazoline-3-one sold by Rohm and Hass Company under the trade name Kathon® CG/ICP. Typical levels of bacteriocides used in the present compositions are about 1 ppm to about 2,000 ppm by weight of the composition, depending on the type of bacteriocide selected. Methyl paraben is especially effective for mold growth in aqueous fabric softening compositions with under 10% by weight of the diester component.

Silicones

Dimethylpolysiloxane (silicone) or modified silicone can be added to the composition of this present invention, in order to enhance the softening property and water-absorbency of the unsaturated quaternary ammonium salt of formula (I)–(III). Dimethypolysiloxane or a modified silicone, having a viscosity of 20–10000 cps at 25° C., is preferred.

Modified silicones useful in the present invention include, for example, polyoxyethylene modified silicone and amino-modified silicone, wherein the amount of the modification is preferably less than 10%.

It is preferable that dimethylpolysiloxane or modified silicones are emulsified with a polyoxyethylene-type non-ionic surfactant or a monoalkylcationic-type or dialkylcationic-type cationic surfactant prior to their use.

Other Optional Components

The present invention can include other optional components conventionally used in textile treatment compositions, for example, colorants, preservatives, optical brighteners, opacifiers, fabric conditioning agents, surfactants, stabilizers such as guar gum, anti-shrinkage agents, anti-wrinkle agents, fabric crisping agents, anti-spotting agents, fungicides, anti-corrosion agents, antifoam agents, and the like.

An optional additional softening agent of the present invention is a nonionic fabric softener material. Typically, such nonionic fabric softener materials have an HLB of from about 2 to about 9, more typically from about 3 to about 7. Such nonionic fabric softener materials tend to be readily dispersed either by themselves, or when combined with other materials such as single-long-chain alkyl cationic surfactant, the materials as set forth hereinafter, use of hotter water, and/or with more agitation. In general, the materials selected should be relatively crystalline, higher melting, (e.g., 50° C. or greater) and relatively water-insoluble.

The level of optional nonionic softener in the solid composition is typically from about 10% to about 40%, preferably from about 15% to about 30%, and the ratio of the optional nonionic softener to the ester quaternary (TEQ) of the present invention is from about 1:6 to about 1:2, preferably from about 1:4 to about 1:2. The level of optional nonionic softener in the liquid composition is typically from about 0.5% to about 10%, preferably from about 1% to about 5%. Preferred nonionic softeners are fatty acid partial esters of polyhydric alcohols, or anhydrides thereof, wherein the alcohol, or anhydride, contains from 2 to about 18, preferably from 2 to about 8, carbon atoms, and each fatty acid moiety contains from about 12 to about 30, preferably from about 16 to about 20 carbon atoms. Typically, such softeners contain from about one to about 3, preferably about 2 fatty acid groups per molecule.

The polyhydric alcohol portion of the ester can be ethylene glycol, glycerol, poly (e.g., di-, tri-, tetra, penta-, and/or hexa-) glycerol, xylitol, sucrose, erythritol, pentaerythritol, sorbitol or sorbitan. Sorbitan esters and polyglycerol monostearate are particularly preferred. The fatty acid portion of the ester is normally derived from fatty acids having from about 12 to about 30, preferably from about 16 to about 20 carbon atoms, typical examples of said fatty acids being lauric acid, myristic acid, palmitic acid, stearic acid and behenic acid.

Highly preferred optional nonionic softening agents employable in the present invention include but are not limited to the sorbitan esters, which are esterified dehydration products of sorbitol and the glycerol esters. Sorbitol, which is typically prepared by the catalytic hydrogenation of glucose, can be dehydrated in well known fashion to form mixtures of 1,4- and 1,5-sorbitol anhydrides and small amounts of isosorbides. An exemplary process is described in U.S. Pat. No. 2,322,821which is incorporated herein by reference. The foregoing types of complex mixtures of anhydrides of sorbitol are collectively referred to herein as "sorbitan". Further, one of ordinary skill in the art will recognize that this "sorbitan" mixture will also contain some free, uncyclized sorbitol.

Preferred sorbitan softening agents can be prepared by esterifying the "sorbitan" mixture with a fatty acyl group in standard fashion, e.g., by reaction with a fatty acid halide or fatty acid. The esterification reaction can occur at any of the available hydroxyl groups, and various mono, di-, etc., esters can be prepared. Mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method is described more filly in MacDonald; "Emulsifiers:" Processing and Quality Control:, *Journal of the American Oil Chemists' Society*, Vol. 45, October 1968. Details, including formulas of the preferred sorbitan esters, can be found in U.S. Pat. No. 4,128,484, which is incorporated herein by reference. Certain derivatives of the preferred sorbitan esters herein, especially the "lower" ethoxylates thereof (i.e., mono-, di-, and tri-esters) wherein one or more of the unesterified —OH groups contain one to about twenty oxyethylene moieties [Tweens®] are also useful in the composition of the present invention. Therefore, for purposes of the present invention, the term "sorbitan ester" includes such derivatives.

For the purposes of the present invention, it is preferred that if sorbitan esters are employed, that a significant amount of di- and tri- sorbitan esters are present in the ester mixture. Ester mixtures having from 20–50% di-ester and 10–35% of tri- and tetra-esters are preferred. Commercially available material, such as sorbitan mono-ester (e.g., monostearate), contains significant amounts of di- and tri-esters and a typical analysis of sorbitan monostearate indicates that it comprises about 27% mono-, 32% di- and 30% tri- and tetra-esters. Commercial sorbitan monostearate therefore is a preferred material. Mixtures of sorbitan stearate and sorbitan palmitate having stearate/palmitate weight ratios varying between 10:1 and 1:10, and 1,5-sorbitan esters are useful. Both the 1,4- and 1,5-sorbitan esters are also useful herein.

Other useful alkyl sorbitan esters for use in the softening compositions herein include sorbitan monolaurate, sorbitan monomyristate, sorbitan monopalmitate, sorbitan monobehenate, sorbitan monooleate, sorbitan dilaurate, sorbitan dimyristate, sorbitan dipalmitate, sorbitan distearate, sorbitan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is preferred that such impurities are present at as low a level as possible.

The preferred sorbitan esters can contain up to about 15% by weight of esters of the $C_{20}$–$C_{26}$ and higher, fatty acids, as well as minor amounts of $C_8$, and lower, fatty esters. Glycerol and polyglycerol esters, especially glycerol, diglycerol, triglycerol, and polyglycerol mono- and/or di-esters, preferably mono-, are preferred herein. Glycerol esters can be prepared from naturally occurring triglycerides by normal extraction, purification and/or interesterification processes or by esterification processes of the type set forth herein before for sorbitan esters. Partial esters of glycerin can also be ethoxylated to form usable derivatives that are included within the term "glycerol esters".

Useful glycerol and polyglycerol esters include mono-esters with stearic, oleic, palmitic, lauric, isostearic, myristic, and/or behenic acids and the diesters of stearic, oleic, palmitic, lauric, isostearic, behenic, and/or myristic acids. Typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols are preferred, the fatty acyl groups typically being those described herein before for the sorbitan and glycerol esters.

The quaternary ammonium salts of the present invention may also be utilized in products other than fabric softening compositions. These products may include hair care formulations, skin care formulations, and the like, for the softening, lubrication, emolliency and condition of said hair and/or skin when applied in effective amounts.

Such hair and skin care compositions incorporating the softening conditioning agents of the present invention can be formulated with any cosmetically acceptable vehicle which is inert to the conditioning agent and to the hair or skin, as the case may be. By "cosmetically acceptable" is meant that the vehicle is inert to the skin or hair and permits easy, even application to the skin or hair of a thin film which contains the reaction product. Such vehicles can comprise any of a large variety of forms, including oil-in-water emulsions, water-in-oil emulsions, anhydrous compositions such as oil-based liquids, slurries, powders or pastes, and aqueous solutions, slurries and pastes, Conditioning compositions in accordance with the present invention preferably contain a total of from about 0.1 wt. % to about 10 wt. % of the indicated mixture of compounds of the formulae I–IV.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearly alcohol, glyceryl ricinoleate, glycerol stearate propane 1,2-diol, butane-1,3-diol, mink oil, cetyl alcohol, stearamidopropyl dimethylamine, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cicosanyl alcohol, behenyl alcohol, cetyl palmitate, silicon oils such as dimethylpolysiloxane, dimethicone copolyols, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, aracis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate;

Solvent such as ethyl alcohol, propylene glycol, water, isopropanol, castor oil, ethylene glycol monoethyl ether, diethylene glycol monobutyl ether, diethylene glycol monoethyl ether, dimethyl sulphoxide, dimethyl fonmamide, tetrahydrofuran; and Humectants, such as glycerine, sorbitol, sodium 2-pyrrolidone-5-carboxylate, soluble collagen, dibutyl phthalate, propylene glycol, gelatin.

Powders can include components such as chalk, talc, Fuller's earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, cellulosics such as hydroxethy cellulose and sodium carboxymethyl cellulose, ethylene glycol monstearate, zinc or magnesium stearate, zinc oxide and magnesium oxide. These components may also be used as thickeners in fluid or semi-fluid compositions.

Examples of additional composition types are found in Encyclopedia of Chemical Technology, Vol. 7, pages 146–150 and 144–160 (John Wiley & Sons, 1979), the disclosure of which is hereby incorporated herein by reference.

Examples of other conventional adjuncts, some of which can also function as vehicles, that may optionally be employed, include volatile and nonvolatile silicones, silicone polymers; preservatives, such as p-hydroxy benzoate esters; humectants, such as butane-1,3-diol, glycerol, sorbitol, polyethylene glycol; stabilizers, such as sodium hydroxide; oils and waxes, such a avocado oil, Evening Primrose oil, mineral oil, petrolatum, sunflower oil, beeswax, ozokerite wax, paraffin wax, lanolin, lanolin alcohol; emollients; thickeners; activity enhancers; colorants, whiteners, fragrances; and bactericides.

When the desired conditioning composition is a solution, one can simply stir together the desired amount of the mixture of compounds of formula (1) together with the solvent, such as water or for instance, a lower alcohol containing 1–6 carbon atoms in which the mixture is soluble, or a mixture of water and such an alcoholic component. A useful embodiment is a solution of 85% active and 15% ethanol. A preferred embodiment is 75% active and 25% propylene glycol.

When the desired composition is in the form of an emulsion, for instance as a cream or lotion, the composition should also contain an emulsifier component which is constituted of one or more emulsifiers chosen to provide the HLB (hydrophilic-lipophilic balance) appropriate to whether the aqueous or oil phase is the continuous phase, and appropriate to the choice of the particular components present. Suitable cosmetically acceptable emulsifiers abound and are well known to the cosmetic chemist. Examples include compounds having a long-chain alkyl or alkylene chain of 12 to 20 carbon atoms substituted with a chain 4 to 20 ethoxy or propoxy units; and glycol or glycerol derivatives substituted with an alkyl or alkylene chain of 12 to 24 carbons atoms. Further examples are found in Encyclopedia of Chemical Technology, Vol. 8, Pages 913–916 (John Wiley & Sons, 1979), which are hereby incorporated herein by reference.

The topical skin conditioner compositions of the invention can be formulated as a fluid, for example in a product such as a lotion, with or without an applicator such as a roll-ball applicator, or a container fitted with a pump to dispense the composition, for example as a cream or mousse, or simply in a non-deformable bottle or squeeze container. Alternatively, the composition of the invention may be semi-solid, for example as a cream, lotion, gel, paste or ointment for use in conjunction with a suitable applicator or simply in a tube or lidded jar. Hair and skin conditioner compositions are preferably flowable liquids (solutions, emulsions or dispersions) although they can be in the form of thickened gels, pastes and the like that can be rubbed into and onto the hair or skin.

The conditioning compositions useful in the present invention will preferably contain in addition substances effective to adjust the pH of the composition to values within desired ranges compatible with the surfaces to which the conditioning agent will be applied. Thus, for instance, it is preferred that the pH of a hair conditioning composition be in the range of about 4.0 to about 5.5 in order to provide proper compatibility with the hair shaft itself. It is preferred that skin conditioning compositions have a pH of about 3.5 to about 5.5 in order to provide proper conditioning to the skin while avoiding irritation that would ensue from pH values that are too low or too high. Suitable agents for adjusting the pH to within these desired limits without otherwise disturbing the desired attributes of the conditioning compositions include citric acid (to adjust the pH downwards) and small amounts of sodium hydroxide (to adjust the pH upwards).

The conditioning compositions can also contain additional adjuvants which enhance the conditioning properties of the compositions and agents which provide fluidity to the composition. As is familiar to those having experience in this field, the conditioning compositions are preferably flowable liquids which retain sufficient viscosity that they do not immediately run off of the surface to which they are applied.

Thus, it is preferred that the conditioning compositions include one or more fatty alcohols, by which is meant compositions of the formula $R^1OH$ wherein $R^1$ represents an alkyl or alkylene group, straight or branched, containing 12–22 carbon atoms and 0, 1 or 2 carbon-carbon double bonds.

The formulation of the compositions is straightforward and well within the skill of those familiar with the manufacture of conditioning compositions. The ingredients are stirred together in a suitable mixing vessel until a homogeneous flowable composition is formed. The composition is then metered into appropriated containers, sealed and available for shipment to the point of purchase.

The resulting conditioning compositions can be used in the manner presently employed with conventional hair conditioning compositions and skin conditioning compositions. For use on the hair, it is adequate to pour an amount generally ranging from about 1 to about 5 grams about the hair, to work it into the hair thoroughly, and then to rinse it from the hair. For skin conditioning compositions, amounts generally used are on the order of 0.5 to 2 fluid ounces which are applied to the skin or applied to the hands and then rubbed onto the skin with any excess amounts of conditioner simply wiped off of the skin. It will be recognized that the appropriate amount to use can readily be ascertained as a function of the conditioning effect imparted by the composition and as a function of the volume of hair or area of skin that is desired to be conditioned.

The invention will now be illustrated by the following nonlimiting examples.

DETERMINATION OF ESTER CONTENT

The following method was used to determine the mono-, di-, and triester content of the trialkanolamines formed.

The sample to the analyzed is dissolved on pyridine, silylated, and analyzed by cool on-column injection capillary gas chromatography with flame ionization detection. The distribution of components is calculated based on the corrected are percent response. The area percent response in corrected based on theoretical flame ionization detector response factors.

Chromatography is carried out on a Chrompack WCOT ulti-metal 10 meter x 0.53 mm column coated with HT SimDist CB phase. The gas chromatograph oven program is 6 minutes at 100° C. initial temperature, ramp at 10° C./Min to 175° C., then ramp at 20° C./Min to 375° C., a held 6 minutes at the final temperature.

EXAMPLE

Process for Preparing 90% Active Softening Composition With TEA Based Esterquat

| Balance of materials - TEEA | | |
|---|---|---|
| BHT | = | 1.42 g |
| Hypophosphorous acid (50% solution) | = | 1.24 g |
| Distilled Tallow or $C_{16}$–$C_{18}$ with | = | 710 g |

| -continued | | |
|---|---|---|
| Balance of materials - TEEA | | |
| $C_{18}$ Unsaturated Fatty Acid | = | |
| Triethanolamine (TEA) | = | 231.8 g |

TEEA (a fatty acid ester amine of TEA) was prepared in a 2L-resin kettle connected to an overhead stirrer, three-ball Snyder column, addition funnel, distillation setup, nitrogen sparge and temperature control. The system was vacuum-leak tested before starting the experiment. Molten fatty acid, antioxidants and hypophosphorous acid were charged to the reaction flask and kept at 65–75° C. under nitrogen. The reaction apparatus was then purged by pulling vacuum to 29" Hg and breaking vacuum with nitrogen three times in order to remove any air in the system. TEA was then added and after addition, the reaction mixture was heated up with a ramp rate of 1.75° C. per minute. As the reaction temperature reached 105° C., vacuum was pulled to 26" Hg and the reaction was continued heating up to 195–200° C. At this temperature and pressure, the reaction was held for approximately 20 minutes. Free fatty acid was approximately 0.07 meq/g. Moisture level should be <0.1% or drying may be required prior to quaternization.

| Balance of materials - Ester quat (TEO) of the present invention | | |
|---|---|---|
| TEEA | = | 306.3 g |
| Isopropanol | = | 41.3 g |
| DMS | = | 62.1 g |
| EDTA (40% solution) | = | 0.26 g |
| BHT | = | 0.21 g |

TEEA was charged into the reactor and heated to 80° C. under nitrogen, and dried for approximately 30 minutes. The dried TEEA was then cooled to 60° C. after which the isopropanol was added (5% batch weight). The heat mantle was then removed and the DMS was added dropwise over a time period of about 20 minutes. The reaction temperature increased from about 50° C. to 85° C. because of the exotherm. The contents of the reactor were then allowed to digest at 85–90° C. for approximately two hours. EDTA and BHT were then added, and the remaining isopropanol (5%) was added to the mixture.

The resultant product had the following characteristics:

| | |
|---|---|
| Appearance: | viscous liquid at room temperature |
| Solvent: | isopropanol (IPA) |
| Activity: | 90% active |
| Color (Gardener scale): | 2 |
| pH (1% in 50/50 IPA:water): | 3–4 |
| Specific Gravity: | 0.978 g/cc |
| Cloud Point: | 38–39° C. |
| Pour Point: | 19–21° C. |
| Water: | 0.5% or less |
| Ester Distribution wt % Mono/di/tri (based on esteramine) | 26.5/59.5/10.5 |

EXAMPLE 2

"Standard" Rinse Cycle Softener Formulation (7.5% Active)

| Raw Materials: | |
| --- | --- |
| Quaternary salt of Example 1 | 8.40% |
| DI-water | 91.60% |
| 1 N HCl | pH 2.7–3.2 |
| Fragrance | q.s |
| Dye/colorant | q.s |
| Anti-microbial | q.s |

Preheat water to between 45 and 60° C. Add the heated water to a suitable vessel and acidify to a pH of 2.7–3.2 with 1 N HCl. Add the warmed quaternary salt of the acidified water while agitating and maintaining a temperature of 45–60° C. Cool the dispersion while agitating. Solubilize fragrance into the softener dispersion at 40° C. Add dye and preservative as desired. Adjust weight with DI-water. Dispersion is storage stable within a temperature range of 4 to 50° C.

EXAMPLE 3

"Ultra" Rinse Cycle Softener Formulation (24% Active)

| Raw Materials: | |
| --- | --- |
| Quaternary salt of Example 1 | 26.80% |
| DI-water | 73.20% |
| 1 N HCl | pH 2.7–3.2 |
| 10% aqueous Calcium Chloride (CaCl$_2$) solution | |
| Fragrance | q.s |
| Dye/Colorant | q.s |
| Anti-microbial | q.s |

Preheated DI-water to 50–60° C. Charge DI-water to mixing vessel and acidify water to a pH to 2.7–3.2 with 1 N HCl. Add the warmed quaternary salt to the acidified water with agitation while maintaining a temperature of 50–60° C. After addition of 73% of active, add CaCl$_2$ solution to the stirring dispersion. Make a second salt addition after 84% of active is added, and a third minor salt addition at completion of actives addition. Continue agitation to insure a smooth, homogeneous dispersion. Cool to 40° C. with agitation. Solublize fragrance into the softener dispersion. Adjust viscosity to the desired level with addition of CaCl$_2$ solution. Add color and preservative. Adjust weight with DI-water. Dispersion is storage stable within a temperature range of 4–50° C. For an even higher level of softening, dispersions containing 28–40% actives can be easily formulated employing techniques similar to those shown above.

EXAMPLE 4

In this example, dispersions of Armosoft® TEQ and Stepantex® VS-90 (a product of Stepan) were compared relative to each other and a national brand of fabric softener using standard methods of Akzo Nobel for evaluating the softening performance of a cationic surfactant. These same methods are based upon typical industry protocols such as ASTM D-3. In each case the cationic surfactants were formulated to produce dispersions of 24% solids (by weight). These dispersions were allowed to age for approximately one week and were then used to treat cotton hand towels. The cotton hand towels were then evaluated by a trained group of 24 panelists. Each panelist was required to make a choice in a pair comparison situation of which treated towel was "softer."

BRIEF DESCRIPTION OF THE DRAWINGS

Figure 1:
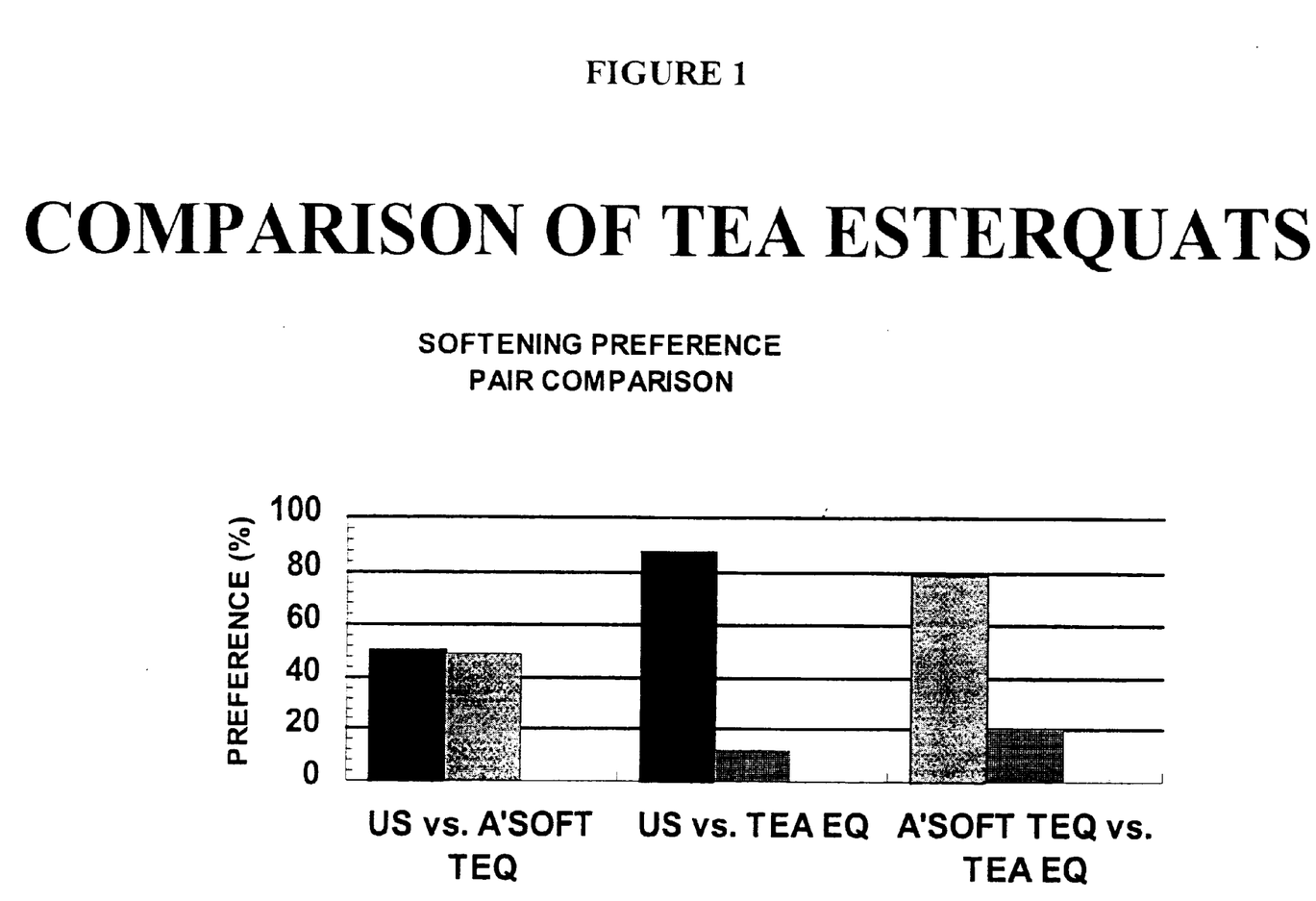

The results of the several tests are shown in summary in FIG. 1 where US is a "national" brand, A'soft TEQ is for the towels treated with Armosoft TEQ of the present invention, and TEA EQ is for the towels treated with the Stepantex dispersion. The data clearly show a preference for the Armsoft TEQ treated towels over those treated with the Stepantex product. Additionally the Armosoft TEQ was judged comparable to the national brand whereas the Stepantex product was judged inferior. All of these results compliment each other, indicating the superior performance of the compositions containing theesterquats produced in accordance with the present invention.

Stepantex is a cationic softener prepared via the reaction of fatty acid with triethanol amine (TEA) and then quaternized with dimethyl sulfate (DMS). Although there are different versions of this molecule the methods of production are similar, but the raw materials may be varied in terms of ration of fatty acid to TEA, the fatty acid source, and other adjuvants which are incorporated in an attempt to reach a more viscosity stable product. In this case the sample evaluated had a fatty acid to TEA ration of roughly 1.72:1. The alkyl chain source was typical of a partially hydrogenated tallow with an acid I.V. of approximately 40 cg/gram. Additionally an alkyl amidopropyl amine quat was added in addition to some triethanol amine (small molecule) quat to enhance formulatability and dispersion stability (these comprising roughly 8% of the product). The esteramine distribution indicated that roughly 46% of the esterquat was of the dialkyl ester type, whereas 30% was of the trialkyl ester type. The balance being composed of the mono ester type. The product was nearly 90% solids by weight. EP 0 550 361 A1 indicates the preparation of esterquats of this type by Stepan.

EXAMPLE 5

Ultra Rinse Cycle Softener Formulation (28% Active)

| Raw Materials: | |
| --- | --- |
| Quaternary salt of Example 1 | 156 g |
| DI-water | 315 g |
| I N HCl | pH 2.7–3.2 |
| 10% aqueous Calcium Chloride (CaCl$_2$) solution | ~20 ml |
| Fragrance | q.s |
| Dye/Colorant | q.s |
| Anti-microbial | q.s |

The DI-water is preheated to 50–60° C. and charged to the mixing vessel and acidified to a pH of 2.7–3.2 with 1N HCl. The molten quaternary salt is then slowly added to the mixing vessel with mixing while the temperature is maintained at about 60° C. Incremental additions of CaCl$_2$ solution are made to control the viscosity during formulation. The mixture is then cooled to 40° C. with agitation wherein the fragrance solubilized into the softener dispersion. The viscosity is then adjusted to the desired level with addition of CaCl$_2$ solution, and color and preservative added. Lastly, the weight is adjusted with DI-water. The dispersion is storage stable within a temperature range of 4–50° C.

EXAMPLE 6

Preparation of Methyl Sulfate Quaternary of Ditallowalkylester of Methoxyethyl Diethanolamine i) Preparation of Methoxyethyldiethanolamine To a two liter autoclave was added (601 g, 8.0 mole) of 2-methoxyethylamine. The autoclave was purged with nitrogen while heating to 70° C. The purge was stopped, the autoclave was closed, and then it was heated to 120° C. (internal pressure was at 18 psig due to nitrogen). Ethylene oxide was added until the reactor pressure reached 25 psig. After 20 minutes, the temperature was increased to 140° C. to initiate the reaction. After initiation, the temperature was increased to 160° C. (Note: The pressure reached 66 psig). At 160° C. ethylene oxide was added over 1.5 hr under pressure until a total of 670 g (15.2 mole) had been added to the reactor. The reaction was then digested for a further 30 minutes and allowed to cool to 140° C. After 40 minutes at 140° C. , the reactor was allowed to slowly cool to ambient temperature. Titration with HCl indicated: neutralization equivalent, 166.7.

ii) Preparation of Ditallowalkylester of Methoxyethyldiethanolamine

Methoxyethyldiethanol amine (95.1 g, 0.584 mole), hypophosphorous acid (1.2 g, 0.4% based on fatty acid), Irganox 1076 (0.15 g, 0.05% based on fatty acid) and Prifac® 7943 (300 g, 1.091 mole) were charged to a 1L round bottomed flask. The reaction mass was then heated to 190° C. over 2.5 hour. Some water distilled during the heating and was collected. The contents of the reaction flask were placed under vacuum for 3 hrs and additional water was collected. The heating source was removed and the contents of the reaction flask were allowed to cool to room temperature before the vacuum was broken with nitrogen. The resultant esteramine analyzed as follows: monoester amine, 5.9%; diesteramine, 89.5%; free fatty acid, 0.019 meq/g; color, 2.1 Gardner; neutralization equivalent, 689.

iii) Methy Sulfate Quaternary of ii).

Ditallowalkylester of methoxyethyldiethanolamine (300 g, 0.435 mole) and isopropanol (15.0 g) were stirred and heated to 80° C. Dimethyl sulfate (50.08 g, 0.397 mole ) was slowly added drop-wise. The reaction mass was digested for three hours before a sample was taken and the free amine checked by wet methods. A second dimethyl sulfate charge was made (3.00 g, 0.0238 mole) and the reaction mass was digested for an additional three hours. The quaternary analyzed as follows: free amine, 0.041 meq/g; amine salt, 0.127 meq/g; pH 2.4; color, 1.0 Gardner; % solids, 95.5%.

EXAMPLE 7

Preparation of Methyl Sulfate Quaternary of Ditallowalkylester of Methoxypropyldiethanolamine i) Preparation of Methoxypropyl Diethanolamine 3-Methoxypropylamine (665.5 g, 7.466 mole) and ethylene oxide (624 g, 14.18 mole) were reacted as described above in the procedure for making methoxyethyldiethanolamine (Example 5 (i)). The material was analyzed and the neutralization equivalent was determined 177.13.

ii) Preparation of Ditallowalkylester of Methoxypropyldiethanolamine

3-Methoxypropyldiethanolamine (311.4 g, 1.757 mole), hypophosphorous acid (3.61 g, 0.4% based on fatty acid), Irganox 1076 (0.45 g, 0.05% based on fatty acid) and Prifac 7943 (903.1 g, 3.284 mole) were reacted as described in the procedure above for making ditallowalkylester of methoxyethyldiethanolamine. The resultant esteramine analyzed as follows: monoester amine, 5.91%; diesteramine, 94.0%; free fatty acid, 0.025 meq/g; color, 2.2 Gardner; neutralization equivalent, 687.

iii) Methyl Sulfate Quaternary of ii)

Ditallowalkylester of methoxypropyldiethanolamine, (781 g, 1.137 mole), isopropanol (78.1 g) and dimethyl sulfate (129.1 g, 1.0231 mole) were reacted as described in the procedure above for making the methyl sulfate quaternary of ditallowalkylester of methoxyethyldiethanolamine. The quaternary analyzed as follows: free amine, 0.036 meq/g; amine salt, 0.170 meq/g; pH, 3.5; color, 3.8 Gardner; % solids, 86.7%.

EXAMPLE 8

Preparation of Methyl Chloride Quaternary

A stirred stainless steel autoclave having a capacity of 2 L was charged with 0.7 moles of the ester amine and 0.58 moles of 2-Propanol. The autoclave was heated to 1 10° C. and continuous stirring maintained at 550 rpm's. Methyl chloride (0.861 moles) was added and the reaction conditions were maintained. The reaction mass was sampled every hour for free amine and amine salt content. After the free amine was less then 0.025 meq/g, the reaction mass was cooled to 70° C., vented and the product removed. Esteramines with high and low triester content were quaternized. The esteramine with the lower triester content, esteramine B, quaternized more rapidly than the one with a higher triestermine content, esteramine A.

| Samples | diesteramine in percent | triesteramine in percent | time of reaction in hours |
|---|---|---|---|
| A | 50 | 35 | 17.0 |
| B | 56 | 11 | 8.5 |

EXAMPLE 9

Preparation of Di(ethyl soy acid ester)2 -hydroxypropyl Methyl Ammonium Methosulfate A. Ester-amine

B.

418.3 grams (1.49 moles) of molten soy fatty acid, 0.41 grams of BHT, 0.41 grams of BHA, and 0.73 grams of 50% solution hypophosphorous acid were charged to a reaction vessel which was connected to an overhead-stirrer, three-ball snyder column, additional funnel, distillation setup, nitrogen sparage and a temperature controller. The mixture was kept at about 70° C. under nitrogen. 143.2 grams (0.88 mole) of N, N-bis(2-hydroxyethyl) isopropanolamine was added. After amine addition, the reaction mixture was heated up with a ramp rate of about 1.7° C. per minute. As the temperature reached 105° C., vacuum was pulled to 26" Hg and the reaction was continued heating up to 195° C. At this temperature and pressure, the reaction was held until free fatty was less than 0.07 meq/g.

B. Ester-quat

In a reaction vessel fitted with temperature control, stirrer, condenser, nitrogen sweep, additional funnel was placed 490.2 grams ester-amine (0.78 moles), 65.9 grams isopropanol. The mixture was heated to about 40° C. under nitrogen. 93.4 grams (0.74 mole) dimethyl sulfate was added dropwise at a rate that the reaction temperature did not exceed 80° C. The reaction was digested for two hours.

EXAMPLE 10

Preparation of Di(ethyl soy acid ester)3-hydroxypropyl Methyl Ammonium Methosulfate A. Ester-amine 355 grams (1.27 moles) of molten soy fatty acid and 0.7 grams of 50% solution hypophosphorous acid were charged to a reaction vessel which was connected to an overhead-stirrer, three-ball snyder column, additional funnel, distillation setup, nitrogen sparage and a temperature controller. The mixture was kept at about 70° C. under nitrogen. 121 grams (0.73 mole) of N,N-bis (2-hydroxyethyl) propanolamine was added. After amine addition, the reaction mixture was heated up with a ramp of about 1.7° C. per minute. As the temperature reached 105° C., vacuum was pulled to 25" Hg and the reaction was continued heating up to 195° C. At this temperature and pressure, the reaction was held for about one hour.

B. Ester-quat

In a reaction vessel fitted with temperature control, stirrer, condenser, nitrogen sweep, additional funnel was placed 341.5 grams (0.55 mole) ester-amine and 68.5 grams isopropanol. The mixture was heated to about 50° C. under nitrogen. 66.5 grams (0.53 moles) dimethyl sulfate was added dropwise at a rate that the reaction temperature did not exceed 80° C. The reaction was digested for two hours.

EXAMPLE 11

In this example, a sample was prepared by reacting split soya fatty acid with triethanol amine and subsequently quaternized with dimethyl sulfate to form the quaternary. This "soya" quaternary contains single, double and triple double bonds in the alkyl chain (C18). The sample number of the product was 1348-22-3.

This product was formulated to produce a softener dispersion of 24% solids by weight as is typical in the applications laboratory. The sample number was 1317–81. The product was allowed to age and viscosity stability was tracked as a function of time and temperature. Results indicate that at higher temperatures the dispersions prepared from this quaternary are unstable with respect to viscosity. Additionally the samples became rancid in terms of odor quality within a week of formulation, even at room temperature. Viscosity data for the dispersions are shown below:

| | Viscosity in cps | | | | | |
|---|---|---|---|---|---|---|
| Temp C. | Day 0 | Day 1 | Day 7 | Day 12 | Day 24 | Day 32 |
| 4 | 87.2 | 90.2 | 91 | 95.2 | 99.2 | 93.5 |
| 25 | 87.2 | 86.7 | 87.7 | 86 | 86 | 86 |
| 40 | 87.2 | 102 | 126 | 138 | 153 | 187 |
| 50 | 87.2 | 111 | 167 | — | — | — |

This sample was not evaluated for softening performance due to its poor viscosity stability and lack of odor stability.

EXAMPLE 12

Esterquat Dispersions Produced from High-Trans Tallow Fatty Acid

Here a laboratory sample of Armosof® TEQ was produced from a tallow fatty acid source that was manipulated to create a high percentage of trans fatty acid. The sample was 1348-28-4.

The product was then formulated as typical in the applications laboratory to create a softener dispersion (1317-88) containing 24% solids by weight. The product was shown to have good viscosity stability over a period of four weeks at temperature from 4 C to 50 C. The viscosity data are given below:

| | Viscosity in cps | | | | | |
|---|---|---|---|---|---|---|
| Temp C. | Day 0 | Day 1 | Day 2 | Day 3 | Day 7 | Day 28 |
| 4 | 43.4 | 39.6 | 42.6 | 49.1 | 47.1 | 49.1 |
| 25 | 43.4 | 36.6 | 40.6 | 39.6 | Used | — |
| 40 | 43.4 | 37.1 | 41.6 | 39.6 | 37.6 | 38.1 |
| 50 | 43.4 | 36.6 | 43.1 | 42.6 | 49.1 | 45.1 |

We claim:

1. A hair conditioning composition which comprises a hair conditioning effective amount of:

(i) a mixture of quaternary compounds of the formulae:

I)

II)

III)

wherein:

X, X' and X" are the same or different and are selected from straight or branched chain, optionally substituted oxyalkylene or polyoxyalkylene groups having from 2–6 carbon atoms, where the oxyalkylene units number from about 1–10; each R group is individually selected from straight or branched chain, optionally substituted alkyl or alkylene groups having from 11 to 23 carbon atoms, Y is and alkylphenyl group or a straight or branched chain optionally substituted $C_1$ to $C_6$ alkyl or alkylene group; and $Z^-$ represents a softener compatible anion; wherein said diester component (II) comprises greater than about 55 wt % and said triester component (III) comprises less than about 25 wt % based on the total amount said quaternary ammonium salt; and (ii) a cosmetically acceptable vehicle having a pH which is compatible with human hair.

2. The composition of claim 1 wherein said mixture of quaternary ammonium compounds is present in an amount of from about 0.1 to about 10 wt % based on the weight of the total composition.

3. The composition of claim 1 wherein said mixture of quaternary ammonium compounds comprises greater than about 60% diester component and less than about 20% triester component.

4. A method for the softening, conditioning and/or lubricating hair which comprises applying to said hair a softening, conditioning and lubricating effective amount of the hair conditioning composition of claim 1.

5. A hair conditioning composition which comprises a hair conditioning effective amount of:
   (i) a mixture of quaternary ammonium compounds of general formula (IV):

$$(R-\overset{O}{\underset{\|}{C}}-X)_nN-(Q)_{4-n} \ Z^-  \qquad (IV)$$

wherein
   n is 1 or 2, R is a $C_5$ to $C_{23}$ straight or branched chain, optionally substituted alkyl or alkenyl group, each X can be the same or different and is selected from straight or branched chain, optionally substituted oxyalkylene or polyoxyalkylene groups having from 2–6 carbon atoms; each Q can be the same or different and is selected from a oxyalkylene or polyoxyalkylene group, or a straight or branched chain, optionally substituted alkyl, alkylene, alkyl phenyl, hydroxyalkyl, or hydroxyalkylene, wherein at least one of said Q groups is a $C_2$ to $C_6$ linear or branched chain oxyalkylene or polyoxyalkylene capped with a $C_1$ to $C_6$ alkyl, or an alkyl phenyl group; and $Z^-$ is a compatible anion; and
   (ii) a cosmetically acceptable vehicle having a pH which is compatible with human hair.

6. The composition of claim 5 wherein said mixture of quaternary ammonium compounds is present in an amount of from about 0.1 to about 10 wt % based on the weight of the total composition.

7. The composition of claim 5 wherein said mixture of quaternary ammonium compounds comprises greater than about 70% diester component.

8. A skin conditioning composition which comprises a skin conditioning effective amount of:
   (i) a mixture of quaternary ammonium compounds of the formulae:

(I)
$$R-\overset{O}{\underset{\|}{C}}-X\diagdown\underset{Y}{\overset{X'H}{\underset{|}{\overset{+}{N}}}}\diagup X''H \quad Z^-$$

(II)
$$R-\overset{O}{\underset{\|}{C}}-X\diagdown\underset{R-\overset{O}{\underset{\|}{C}}-X'}{\overset{X''H}{\underset{|}{\overset{+}{N}}}}\diagup Y \quad Z^-$$

(III)
$$R-\overset{O}{\underset{\|}{C}}-X'\diagdown\underset{R-\overset{O}{\underset{\|}{C}}-X'}{\overset{X''-C-R}{\underset{|}{\overset{+}{N}}}}\diagup Y \quad Z^-$$

wherein:
   X, X' and X" are the same or different and are selected from straight or branched chain, optionally substituted oxyalkylene or polyoxyalkylene groups having from 2–6 carbon atoms, where the oxyalkylene units number from about 1–10; each R group is individually selected from straight or branched chain, optionally substituted alkyl or alkenyl groups having from 11 to 23 carbon atoms, Y is and alkylphenyl group or a straight or branched chain optionally substituted $C_1$ to $C_6$ alkyl or alkylene group; and $Z^-$ represents a softener compatible anion; wherein said diester component (II) comprises greater than about 55 wt % and said triester component (III) comprises less than about 25 wt % based on the total amount said quaternary ammonium salt; and
   (ii) a cosmetically acceptable vehicle having a pH which is compatible with human skin.

9. The composition of claim 8 wherein said mixture of quaternary ammonium compounds is present in an amount of from about 0.1 to about 10 wt % based on the weight of the total composition.

10. The composition of claim 8 wherein said mixture of quaternary ammonium compounds comprises greater than about 60% diester component and less than about 20% triester component.

11. A method for the softening, conditioning and/or lubricating skin which comprises applying to said skin a softening, conditioning and lubricating effective amount of the skin conditioning composition of claim 8.

12. A skin conditioning composition which comprises a skin conditioning effective amount of:
   (i) a mixture of quaternary ammonium compounds of the formulae: general formula (IV):

$$(R-\overset{O}{\underset{\|}{C}}-X)_nN-(Q)_{4-n} \ Z^- \qquad (IV)$$

wherein
   n is 1 or 2, R is a $C_5$ to $C_{23}$ straight or branched chain, optionally substituted alkyl or alkenyl group, each X can be the same or different and is selected from straight or branched chain, optionally substituted oxyalkylene or polyoxyalkylene groups having from 2–6 carbon atoms; each Q can be the same or different and is selected from a oxyalkylene or polyoxyalkylene group, or a straight or branched chain, optionally substituted alkyl, alkylene, alkyl phenyl, hydroxyalkyl, or hydroxyalkylene, wherein at least one of said Q groups is a $C_2$ to $C_6$ linear or branched chain oxyalkylene or polyoxyalkylene capped with a $C_1$ to $C_6$ alkyl, or an alkyl phenyl group; and $Z^-$ is a compatible anion; and (ii) a cosmetically acceptable vehicle having a pH which is compatible with human skin.

13. The composition of claim 12 wherein said mixture of quaternary ammonium compounds is present in an amount of from about 0.1 to about 10 wt % based on the weight of the total composition.

14. The composition of claim 12 wherein said mixture of quaternary ammonium compounds comprises greater than about 70% diester component.

* * * * *